(12) United States Patent
Crawford et al.

(10) Patent No.: US 10,099,927 B2
(45) Date of Patent: Oct. 16, 2018

(54) DERIVATIZATION OF CARBON

(71) Applicant: SCHLUMBERGER TECHNOLOGY CORPORATION, Sugar Land, TX (US)

(72) Inventors: Lynne Crawford, Harlow (GB); Nathan Lawrence, Wyton (GB); Timothy Jones, Cottenham (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 188 days.

(21) Appl. No.: 14/365,591

(22) PCT Filed: Dec. 21, 2012

(86) PCT No.: PCT/IB2012/057617
§ 371 (c)(1),
(2) Date: Jun. 13, 2014

(87) PCT Pub. No.: WO2013/093883
PCT Pub. Date: Jun. 27, 2013

(65) Prior Publication Data
US 2014/0353175 A1 Dec. 4, 2014

(30) Foreign Application Priority Data
Dec. 21, 2011 (GB) .................................. 1122043.1

(51) Int. Cl.
*C01B 31/02* (2006.01)
*C01B 31/04* (2006.01)
(Continued)

(52) U.S. Cl.
CPC .............. *C01B 31/02* (2013.01); *B82Y 30/00* (2013.01); *B82Y 40/00* (2013.01);
(Continued)

(58) Field of Classification Search
CPC ...................................................... C01B 21/02
See application file for complete search history.

(56) References Cited

U.S. PATENT DOCUMENTS 3,780,575 A  12/1973  Urbanosky
3,859,851 A   1/1975  Urbanosky
(Continued)

FOREIGN PATENT DOCUMENTS

WO  2004063743 A1  7/2004
WO  2005028174 A2  3/2005
(Continued)

OTHER PUBLICATIONS

Temel, Gokhan et al., Polym. Bull 2013, vol. 70 pp. 3563-3574 (Sep. 2013) (Year: 2013).*
(Continued)

*Primary Examiner* — Jill Warden
*Assistant Examiner* — Matthew Krcha

(57) ABSTRACT

A process for derivatization of an elemental carbon surface comprising exposing the carbon surface to a reaction mixture containing a thiol and a free radical initiator, and inducing decomposition of the initiator to free radicals so that moieties from the thiol become covalently attached to the carbon surface. The process can derivatize carbon with a redox active compound having a functional group which can be converted electrochemically between reduced and oxidized forms. Such derivatized carbon may be used in an electrode of an electrochemical sensor.

11 Claims, 5 Drawing Sheets

(51) Int. Cl.
 G01N 27/30 (2006.01)
 G01N 27/48 (2006.01)
 B82Y 30/00 (2011.01)
 B82Y 40/00 (2011.01)
(52) U.S. Cl.
 CPC .......... *C01B 31/0273* (2013.01); *C01B 31/04* (2013.01); *C01B 31/0484* (2013.01); *G01N 27/302* (2013.01); *G01N 27/308* (2013.01); *G01N 27/48* (2013.01)

(56) References Cited

U.S. PATENT DOCUMENTS

| | | | |
|---|---|---|---|
| 4,994,671 | A | 2/1991 | Safinya et al. |
| 5,223,117 | A | 6/1993 | Wrighton et al. |
| 7,125,533 | B2 | 10/2006 | Khabashesku et al. |
| 2007/0280876 | A1 | 12/2007 | Tour et al. |
| 2009/0178921 | A1 | 7/2009 | Lawrence et al. |
| 2010/0009432 | A1* | 1/2010 | Lee ................. B82Y 30/00 435/287.2 |

FOREIGN PATENT DOCUMENTS

| | | |
|---|---|---|
| WO | 2005066618 A1 | 7/2005 |
| WO | 2010001082 A1 | 1/2010 |
| WO | 2010106404 A2 | 9/2010 |

OTHER PUBLICATIONS

Zabihi, Omid et al., RSC Adv., vol. 5 pp. 98692-98699 (2015) (Year: 2015).*
Akbar, et al., "Synthesis of polyethylene-grafted multiwalled carbon nanotubes via a peroxide-initiating radical coupling reaction adn by using well-defined TEMP and thiol end-functionalized polyethylenes", Journal of Polymer Science: Part A Polymer Chemistry, vol. 49, 2011, pp. 957-965.
Baughman, et al., "Carbon nanotube actuators", Science, vol. 284, No. 5418, May 1999, pp. 1340-1344.
Calvert, "Nanotube composites: A recipe for strength", Nature, vol. 399, No. 6733, May 20, 1999, p. 210-211.
Campidelli, et al., "Functionalization of Carbon Nanotubes for Nanoelectronic and Photovoltaic Applications", John Wiley & Sons, Ltd., Chichester, West Sussex, United Kingdom, 2010, pp. 33-364.
Che, et al., "Carbon nanotubule membranes for electrochemical energy storage and production", Nature, vol. 393, No. 6683, May 28, 1998, pp. 346-348.
Cochet, et al., "Synthesis of a new polyaniline/anotube composite: "in-situ" polymerisation and charge transfer through site-selective interaction", Chem. Commun., vol. 16, 2001, pp. 1450-1451.
Collins, et al., "Nanotube Nanodevice", Science, vol. 278, Oct. 3, 1997, pp. 100-102.
De Heer, et al., "A Carbon Nanotube Field-Emission Electron Source", Science, vol. 270, Nov. 17, 1995, pp. 1179-1180.
Downard, "Electrochemically Assisted Covalent Modification of Carbon Electroaysis", Electroanaysis, vol. 12, No. 14, 2000, pp. 1085-1096.
Fan, et al., "Synthesis, characterizations, and physical properties of carbon nanotubes coated by conducting polypyrrole", Journal of Applied Polymer Science, vol. 74, Issue 11, Dec. 9, 1999, pp. 2605-2610.
Gebhardt, et al., "A Novel Diameter-Selective Functionalization of SWCNTs with Lithium Alkynylides", European Journal of Organic Chemistry, vol. 2010, Issue 8, Jan. 29, 2010, pp. 1494-1501.
Graupner, et al., "Chapter 16: Functionalization of Single-Walled Carbon Nanotubes: Chemistry and Characterization", Oxford Handbook of Nanoscience and Technology, vol. 1, 2010, pp. 508-548.
Graupner, et al., "Nucleophilic-Alkylation-Reoxidation: A Functionalization Sequence for Single-Wall Carbon Nanotubes", Journal of the American Chemical Society, vol. 128, Issue 20, May 2, 2006, pp. 6683-6689.
Hauke, et al., "Chapter 6: Covalent Functionalization of Carbon Nanotubes", Carbon Nanotubes and related Structures—Synthesis, Characterization, Functionalization, and Applications, 2010, pp. 135-198.
Hirsch, et al., "Chapter 1. Functionalization of Carbon Nanotubes", Functional Organic Materials: Syntheses, Strategies and Applications, Wiley-VCH Verlag GmbH & Co. KGaA, Weinheim, Germany, Jan. 16, 2007.
Iijima, et al., "Single-shell carbon nanotubes of 1-nm diameter", Nature, vol. 363, No. 6430, Jun. 17, 1993, pp. 603-604.
Kanungo, et al., "Suppression of Metallic Conductivity of Single-Walled Carbon Nanotubes by Cycloaddition Reactions", Science, vol. 323, No. 5911, Jan. 2009, pp. 234-237.
Kong, et al., "Controlled Functionalization of Multiwalled Carbon Nanotubes by in Situ Atom Transfer Radical Polymerization", Journal of the American Chemical Society, vol. 126 Issue 2, Dec. 24, 2003, pp. 412-413.
Kroto, et al., "C60: Buckminsterfullerene", Nature, vol. 318, Nov. 14, 1985, pp. 162-163.
Leventis, et al., "Derivatised carbon powder electrodes: reagentless pH sensors", Talanta, vol. 63, No. 4, Jul. 8, 2004, pp. 1039-1051.
Liu, et al., "Fullerene Pipes", Science, vol. 280, 1998, pp. 1253-1256.
Liu, et al., "Preparing a Styrenic Polymer Composite Containing Well-Dispersed Carbon Nanotubes: Anionic Polymerization of a Nanotube-Bound p-Methylstyrene", Macromolecules, vol. 37, No. 2, 2004, pp. 283-287.
Adams, et al., "Preparation and Characterization of Sulfonic Acid-Functionalized Single-Walled Carbon Nanotubes", Physica E., vol. 41, Issue: 4, Feb. 2009, pp. 723-728.
McCarthy, et al., "Microscopy studies of nanotube-conjugated polymer interactions", Synthetic Metals, vol. 12, Issues 1-3, Mar. 15, 2001, pp. 1225-1226.
Modi, et al., "Miniaturized gas ionization sensors using carbon nanotubes", Letters to Nature, Nature, vol. 424, Jul. 10, 2003, pp. 171-174.
O'Connell, et al., "Reversible water-solubilization of single-walled carbon nanotubes by polymer wrapping", Chemical Physics Letters, vol. 342, Issues 3-4, Jul. 13, 2001, pp. 265-271.
Pan, et al., "Very long carbon nanotubes", Nature, vol. 394, No. 6694, Aug. 13, 1998, p. 631-632.
Pandurangappa, et al., "Homogeneous chemical derivatisation of carbon particles: a novel method for functionalising carbon surfaces", Analyst, vol. 127, No. 12, 2002, pp. 1568-1571.
Pandurangappa, et al., "Physical adsorption of N,N'-diphenyl-p-phenylenediamine onto carbon particles: Application to the detection of sulfide", Analyst, vol. 128, 2003, pp. 473-479.
Peng, et al., "Functional Covalent Chemistry of Carbon Nanotube Surfaces", Advanced Materials, vol. 21, Issue 6, Feb. 9, 2009, pp. 625-642.
Qin, et al., "Polymer Brushes on Single-Walled Carbon Nanotubes by Atom Transfer Radical Polymerization of n-Butyl Methacrylate", Journal of the American Chemical Society, vol. 126, Issue 1, Dec. 10, 2003, pp. 170-176.
Riggs, et al., "Optical Limiting Properties of Suspended and Solubilized Carbon Nanotubes", The Journal of Physical Chemistry B, vol. 104, No. 30, 2000, pp. 7071-7076.
Singh, et al., "Organic functionalisation and characterisation of single-walled carbon nanotubes", Chem. Soc. Rev., vol. 38, 2009, pp. 2214-2230.
Syrgiannis, et al., "Covalent Sidewall Functionalization of SWNTs by Nucleophilic Addition of Lithium Amides", European Journal of Organic Chemistry, vol. 2008, Issue 15, May 2008, pp. 2544-2550.
Tasis, et al., "Chemistry of Carbon Nanotubes", Chem. Rev., vol. 106, 2006, pp. 1105-1136.
Viswanathan, et al., "Single-Step in Situ Synthesis of Polymer-Grafted Single-Wall Nanotube Composites", Journal of the American Chemical Society, vol. 125, No. 31, 2003, pp. 9258-9259.
Wildgoose, et al., "Chemically Modified Carbon Nanotubes for Use in Electroanalysis", Microchim. Acta, vol. 152, No. 3, 2006, pp. 187-214.

(56) References Cited

OTHER PUBLICATIONS

Wong, et al., "Covalently functionalized nanotubes as nanometre-sized probes in chemistry and biology", Nature, vol. 394, Jul. 2, 1998, pp. 52-55.

Wunderlich, et al., "Preferred Functionalization of Metallic and Small-Diameter Single-Walled Carbon Nanotubes by Nucleophilic Addition of Organolithium and -Magnesium Compounds Followed by Reoxidation", Chemistry—A European Journal, vol. 14, Issue 5, Feb. 8, 2008, pp. 1607-1614.

Yao, et al., "Polymerization from the Surface of Single-Walled Carbon Nanotubes—Preparation and Characterization of Nanocomposites", Journal of the American Chemical Society, vol. 125, Issue 51, Dec. 2, 2003, pp. 16015-16024.

Zanella, et al., "Deposition of Gold Nanoparticles onto Thiol-Functionalized Multiwalled Carbon Nanotubes", Journal of Physical Chemistry B., vol. 109, No. 34, 2005, pp. 16290-16295.

Ye, et al., "Electrocatalytic O2 Reduction at Glassy Carbon Electrodes Modified with Dendrimer-Encapsulated Pt Nanoparticles", J. Am. Chem. Soc., vol. 127, No. 13, 2005, pp. 4930-4934.

Antoniadou, et al., "Anion exchange activity of electrochemically bonded ethylene diamine on carbon fibres", Journal of Applied Electrochemistry, vol. 22, 1992, pp. 1060-1064.

Hayes, et al., "Preservation of NADH Voltammetry for Enzyme-Modified Electrodes Based on Dehydrogenase", Anal. Chem. vol. 71, 1999, pp. 1720-1727.

Seibold, et al., "Structure of Ferrocene", Physical Chemistry Labratory, Oxford University, Aug. 11, 1955, pp. 1967-1968.

Wildgoose, et al., "Graphite powder derivatised with poly-L-cysteine using "building-block" chemistry—a novel material for the extraction of heavy metal ions," J. Mater. Chem., No. 15, 2005, pp. 2375-2382.

Allongue, et al., "Covalent Modification of Carbon Surfaces by Aryl Radicals Generated from the Electrochemical Reduction of Diazonium Salts", J. Am. Chem. Soc., No. 119, 1997, pp. 201-207.

Deinhammer, et al., "Electrochemical oxidation of amine-containing compounds: a route to the surface modification of glassy carbon electrodes", Langmuir, vol. 10, No. 4, 1994, pp. 1306-1313.

Sola, et al., "Unprecedented 1,3-Diaza[3]ferrocenophane Scaffold as Molecular Probe for Anions", J. Inorg. Chem., vol. 50, 2011, pp. 4212-4220.

Lawrence, et al., "Selective determination of thiols: a novel electroanalytical approach", Analyst, J. of the Royal Society of Chemistry, vol. 125, 2000, pp. 661-663.

Gonsalves, et al., "Ferrocene-Containing Polyamids and Polyureas", J. Am. Chem. Soc., vol. 106, 1984, pp. 3862-3863.

Jeroschewski, et al., "Galvanic Sensor for Determination of Hydrogen Sulfide", Electroanalysis, vol. 6, 1994, pp. 769-772.

Andrieux, et al., "Derivatization of Carbon Surfaces by Anodic Oxidation of Arylacetates. Electrochemical Manipulation of the Grafted Films", J. Am. Chem. Soc., vol. 119, 1997, pp. 4292-4300.

Guo, et al., "Modification of a Glassy Crabon Electrode with Diols for the Suppression of Electrode Fouling in Biological Fluids", Chem. Pharm. Bull., vol. 44, No. 4, pp. 860-862.

International Search Report and Written Opinion issued in related PCT application PCT/IB2012/057617 on Jun. 3, 2013, 11 pages.

Search Report issued in related GB application 1122043.1 on Sep. 14, 2012, 4 pages.

* cited by examiner

DERIVATIZATION OF CARBON

CROSS-REFERENCE TO RELATED APPLICATIONS

This application claims priority as a 35 USC 371 application to PCT application PCT/IB2012/057617 filed 21 Dec. 2012, which claims priority to GB application 1122043.1 filed 21 Dec. 2011. The disclosures of both applications above are incorporated by reference herein in their entireties.

BACKGROUND

Derivatization of carbon surfaces, i.e. the covalent attachment of molecules to the surface of elemental carbon, has attracted considerable interest in recent years, in particular in connection with attaching molecules to carbon nanotubes.

The derivatization of carbon may be carried out for a range of purposes which include modification of the surface properties of a carbon substrate, preparation of carbon-epoxy composites and attaching a molecule to a carbon electrode so that it can take part in an electrochemical reaction in an electrochemical sensor or an electrochemical catalyst.

Traditionally, carbon surfaces were modified by vigorous oxidation on the surface leading to the formation of carboxylic, quinonic, ketonic or hydroxylic groups, which were then reacted further with the target molecule. This aggressive process was difficult to control.

A number of procedures have been described for electrochemical induced derivatization leading to the formation of a single covalent bond between a carbon electrode and a moiety which becomes attached. There have also been a number of disclosures of routes for derivatization of carbon, without electrochemistry. These include the homogeneous reduction of diazonium compounds in reducing media—see Pandurangappa et al Analyst, vol 127, page 1568 (2002) and Leventis et al, Talanta vol 63, page 1039 (2004). Also in this category is WO2005/066618 (Schlumberger) which describes the diazocoupling of anthraquinonyl and nitrophenyl groups onto carbon nanotubes by means of the reduction of diazonium salts. WO2010/106404 teaches exposing the carbon to a reaction mixture in which a reactive carbene is transiently formed by reaction between a precursor and an extremely strong base.

SUMMARY

This summary is provided to introduce a selection of concepts that are further described below. This summary is not intended to be used as an aid in limiting the scope of the subject matter claimed.

According to a first aspect of the subject matter disclosed by this application, a process for derivatization of an elemental carbon surface comprises exposing the carbon surface to a reaction mixture containing a thiol (also termed a mercaptan) and a free radical initiator.

The reaction can be depicted in general terms as

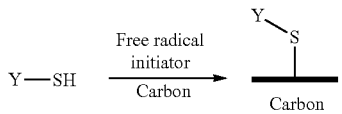

Energy may be supplied to decompose the free radical initiator and thereby release free radicals to bring about the reaction. This may be done by exposure to light, such as an ultra violet light source, or may be done by heating to a moderate temperature.

The moiety Y—S-becomes covalently attached to the carbon surface. Embodiments of this process have the advantage that the reaction can be performed as a one-step process under mild conditions and that the reaction mixture remains a mobile fluid as reaction takes place. This is a versatile process: a considerable range of molecules can be attached to elemental carbon by this route.

A second aspect of the subject matter disclosed herein provides elemental carbon having molecules attached to it through sulfur atoms which are covalently bound to the molecules and to the elemental carbon.

There are numerous circumstances where it is desired to immobilise a molecule on a rigid surface and this process may be used when the objective is to immobilise a molecule onto a solid substrate. Moreover, this derivatization reaction is a way to immobilise a wide range of molecules onto a conductive surface, namely elemental carbon, and the process may be used to immobilise a redox active compound, that is to say a compound having at least one functional group which can be converted electrochemically between reduced and oxidized forms, which can subsequently take part in an electrochemical reaction. This electrochemical redox reaction may be useful in an electrochemical sensor for the determination of pH, hydrogen sulfide or other species for example in a manner as described in WO 2005/66618, the disclosure of which is incorporated herein by reference.

So in another aspect the present disclosure provides an electrochemical sensor electrode comprising elemental carbon having a redox-active compound attached thereto through sulfur atoms covalently bound to said compound and to the elemental carbon. Such a sensor may be a constituent part of measuring apparatus which also has means to apply voltage to the electrode and measure current flow.

Such apparatus may be used for determining presence or concentration of an analyte, and in a further aspect the subject matter disclosed by this application provides a method of determining presence or concentration of an analyte in a liquid, comprising contacting the liquid with at least two electrodes, one of which is an electrode comprising elemental carbon having a redox-active species attached thereto through sulfur atoms covalently bound to said species and to the elemental carbon, and carrying out electrochemical measurement with the electrodes. The liquid may be an aqueous solution but it may also be a non-aqueous liquid such as acetonitrile. A method of determining analyte concentration may comprise applying a potential to the sensor electrode(s) in a sweep over a range sufficient to bring about at least one oxidation and/or reduction of the redox active compound; measuring potential or potentials corresponding to one or more said oxidation and/or reductions; and then processing the measurements to give a determination of analyte concentration.

It will thus be appreciated that embodiments of the derivatization reaction may be used to attach a range of molecules to various forms of elemental carbon in solid form, which may be a particulate solid form, including graphite and carbon nanotubes which may then be immobilised on electrodes and used in electrochemical sensors. It is also possible to carry out the reaction directly onto carbon electrodes.

Within the broad range of possibilities, the molecules which are attached to carbon may be aromatic quinones or aromatic nitro compounds which have previously been disclosed for use in electrochemical sensors. It is also possible by means of the present derivatization reaction to attach a moiety containing ferrocene to act as a reference or to take part in reaction.

DETAILED DESCRIPTION

Figure 1:
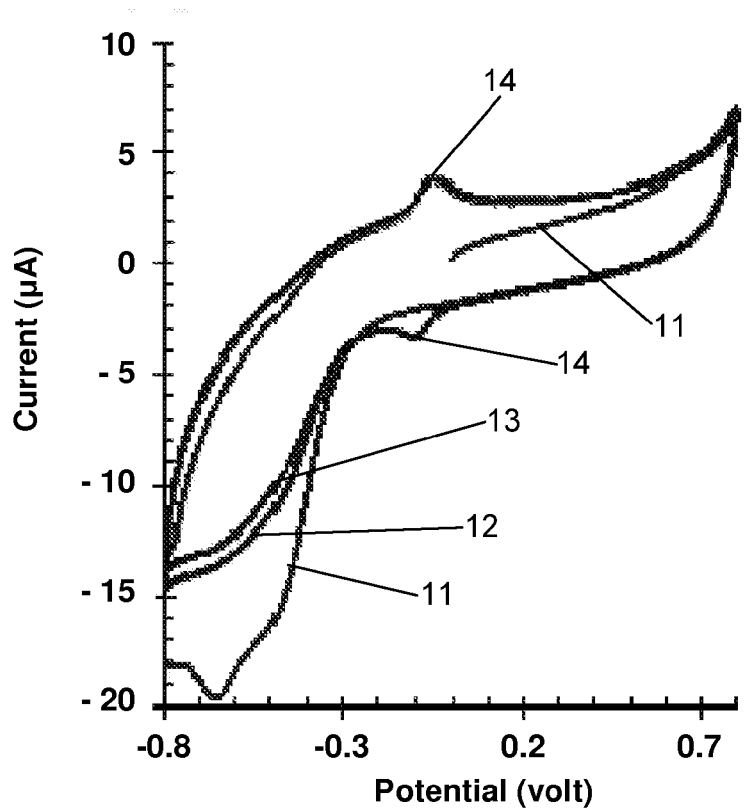
FIGS. 1 and FIG. 2 show the results of cyclic voltammetry in Example 1.

Carbon to be derivatized is exposed to a thiol, variously referred to as a mercaptan, of the general formula Y—SH in the presence of free radicals supplied by an initiator. The reaction may be carried out with the thiol and the free radical initiator in solution or dispersed as a suspension in a liquid. In some embodiments the the thiol and the free radical initiator are in solution in an aprotic solvent which is anhydrous.

The free radical initiator will generally be a compound which decomposes under mild conditions to form free radicals. A number of such compounds are available and may be compounds known for use as free radical initiators of polymerisation reactions.

One class of such materials are azo compounds having a general formula R—N=N—R. These can decompose on heating to liberate R. free radicals and nitrogen. Another class of such molecules is organic peroxides which rupture at the oxygen to oxygen bond. This may be followed by decomposition to more stable carbon centred free radicals.

In some embodiments, the thiol and the free radical initiator are in stoichiometric quantities, or there is an excess of the free radical initiator, so as to bring about complete reaction of the thiol. The relative ratio of the elemental carbon to be derivatized and the thiol to be attached to it may vary considerably. The amount of the thiol may be less than the theoretical amount required to attach to all possible binding sites on the surface of the elemental carbon. Possibly it is not more than 10% or not more than 5% the theoretical amount required to attach to all possible binding sites on the surface of the elemental carbon and it may possibly be much less than this.

The elemental carbon may have a variety of forms including graphite powder, glassy carbon, carbon fibres, carbon black or carbon paste, boron doped diamond and carbon epoxy. A further form of carbon which may be derivatized is the carbon nanotube (CNT) which was discovered in 1991. The structure of carbon nanotubes approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other. Yet another form of carbon which may be derivatized is graphene which may be in the form of graphene flakes and after derivatization these may be immobilized on a conductive substrate. All of these forms of carbon are carbon in a solid form, which may be a particulate solid, or contain carbon in a solid form. The elemental carbon may be conductive and may be for use in an electrode. Forms of conducting carbon used in electrode manufacture are glassy carbon, carbon fibres, carbon black, various forms of graphite, carbon paste, boron doped diamond and carbon epoxy. Carbon nanotubes may also be used as part of an electrode and may be immobilized on the surface of another form of conducting carbon.

Elemental carbon which has been derivatized by the attachment of a molecular species may be used for a variety of purposes. In particular, the Y—S— moiety which becomes attached to carbon may be such that it can undergo electrochemical reduction or oxidation, so that the derivatized carbon can be used in an electrochemical sensor, for example in the manner described in WO 2005/66618, the disclosure of which is incorporated herein by reference. A reversible oxidation and reduction which can be monitored by voltammetry is particularly useful. In some embodiments this may be preceded by an initial irreversible alteration of the covalently attached moiety to form a species which is still covalently attached to the carbon substrate and can undergo reversible electrochemical reduction and oxidation.

The moiety Y—S— which becomes attached to an elemental carbon surface may comprise an aromatic group such as a phenyl group, a condensed aromatic ring system such as napthyl or anthracenyl or an aromatic ring connected to a vinyl group such as a styryl group. An aromatic group may include one or more hetero atoms and thus be a heterocyclic group or a condensed heterocyclic group. This attached moiety may bear one or more substituents which are functional groups able to undergo electrochemical redox reaction. such as a nitro group or two keto groups as in a quinone. Aromatic compounds which have two groups convertible between a reduced hydroxyl form and an oxidized keto form by a two electron, two proton reaction have been previously been found to be particularly suitable as pH sensitive redox active species: anthraquinone is a common example.

Use of a nitro-substituted aromatic moiety as precursor of a redox-active compound was disclosed in WO2010/001082. By application of sufficient voltage some of the nitro groups can be irreversibly reduced electrochemically to hydroxylamino or nitroso groups after which the reduced group displays a pH sensitive reversible redox conversion between a hydroxylamino group and a nitroso group. In the event that this nitroso-/hydroxylamino-substituted moiety becomes depleted while some of its nitro substituted precursor remains available, a voltage pulse can be applied to bring about irreversible reduction of some more of the nitro-substituted precursor.

Another possibility is that a Y—S— moiety may comprise a ferrocenyl group, which is also a group capable of undergoing redox reaction as has been pointed out in WO2005/66618 and elsewhere. Derivatization to attach a ferrocene may be carried out using a thiol of formula Fc-X—SH where Fc denotes a ferrocene or substituted ferrocene and X denotes a linking group which may comprise an aliphatic chain and/or an aromatic ring.

Embodiments of the derivatization process will now be described with reference to the accompanying drawings and the following Examples:

EXAMPLE 1

Derivatization of graphite powder was carried out using commercially available (3-nitrobenzyl)mercaptan and the free radical initiator 2,2'-Azobis(2-methylpropionitrile) also known as azobisisobutyronitrile and abbreviated to AIBN. The reaction can be depicted as

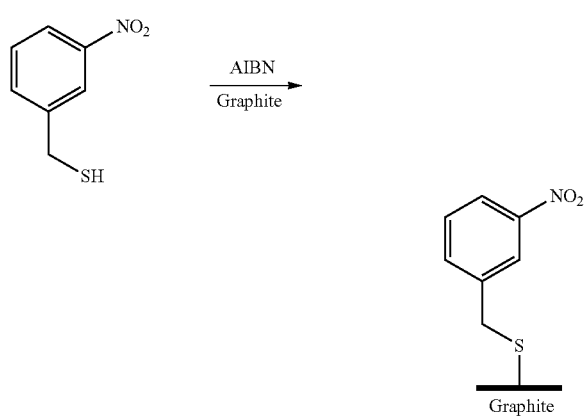

(3-Nitrobenzyl)mercaptan also termed 3-nitrobenzyl thiol (208 mg, 1.23 mmol) was dissolved in anhydrous toluene (1 ml) and 2,2'-azobis(2-methylpropionitrile) (AIBN; 20 mg, 0.12 mmol) and graphite powder (35 mg) added and the suspension heated at 85° C. for 4.5 hr. The derivatized graphite was collected, and washed sequentially with toluene, N,N'-dimethylformamide, de-ionised water and methanol and then dried. The same experimental procedure was also carried out using carbon nanotubes in place of graphite.

The derivatized graphite and derivatized carbon nanotubes were both examined electrochemically to confirm that derivatization had taken place. In each case, the derivatized carbon was dispersed in dichloromethane at a concentration of 1 mg/mL. A 20 µL aliquot of this suspension was spread onto the surface of a glassy carbon electrode and allowed to dry. The electrode was then used as the working electrode in a standard three electrode electrochemical cell, using a stainless steel rod (3 mm diameter, GoodFellow) provided the counter electrode and a saturated calomel electrode (SCE, Radiometer, Copenhagen) acted as the reference. The electrodes were placed in pH7 buffer as electrolyte and cyclic voltammetry was carried out using a µAutolab or a PGSTAT 30 potentiostat (Ecochemie, Netherlands).

Figure 2:
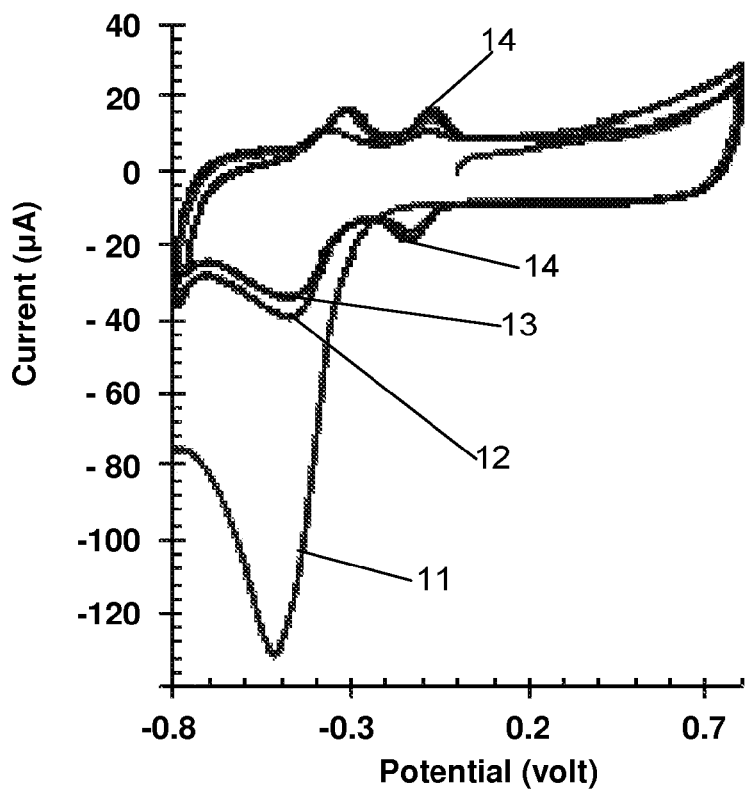

The resulting cyclic voltammetric responses obtained for (3-nitrobenzyl)mercaptan attached to graphite and to carbon nanotubes are shown in FIGS. 1 and 2 respectively.

The potential was swept oxidatively from 0.0V to +0.8V, reversed and swept back to −0.8V and finally returned to 0.0V. This procedure was repeated three times. The voltammetric data for both forms of carbon show no discernable redox couples on the initial oxidative sweep but a single large reduction wave at ca. −0.4V on the first reductive sweep denoted by reference 11, attributed to irreversible reduction of the nitro group to a hydroxylamino group. The second cycle 12 and the third cycle 13 were almost indistinguishable and showed the emergence of new reduction and oxidation waves at −0.1 V denoted by reference 14 and attributed to the reversible reduction of the hydroxylamine group to a nitroso group. This is consistent with reported results for voltammetry of an aromatic nitro group and confirms that the procedure of Example 1 had attached the (3-nitrobenzyl)mercaptan both to graphite and to nanotubes.

EXAMPLE 2

Derivatization of graphite powder was carried out using 4-nitrobenzenethiol as shown:

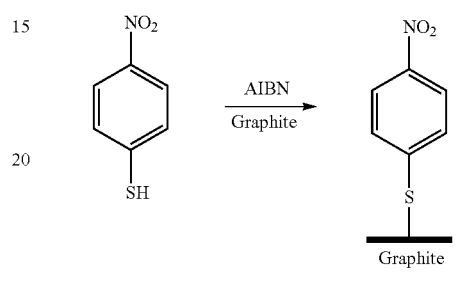

4-Nitrobenzenethiol, also termed 4-nitrophenylthiol or 4-nitrophenyl mercaptan, (technical grade 80%; 125 mg, 0.8 mmol) and graphite powder (75 mg) were added to anhydrous 1,2-dichloroethane (2 ml) and the suspension purged with nitrogen for 10 mins. AIBN (75 mg, 0.45 mmol) was added and the suspension heated at 50° C. for 16 hr. The graphite was collected, washed sequentially with 1,2-dichloroethane, acetone, de-ionised water and methanol. The derivatized graphite powder was then dried.

The derivatized graphite was examined electrochemically in the same manner as in Example 1 to confirm that derivatization had taken place. The electrolyte was 0.1 M HCl and the results of cyclic voltammetry are shown in FIG. 2. As with (3-nitrobenzyl)mercaptan in Example 1, a broad reductive peak current attributed to reduction of the nitro group to hydroxylamino was observed at −0.3V and after the first cycle a new redox wave emerges at +0.20V, indicating successful attachment to the surface of the graphite.

EXAMPLE 3

Attachment of 6-(ferrocenyl)hexane thiol to graphite powder. This reaction can be depicted as

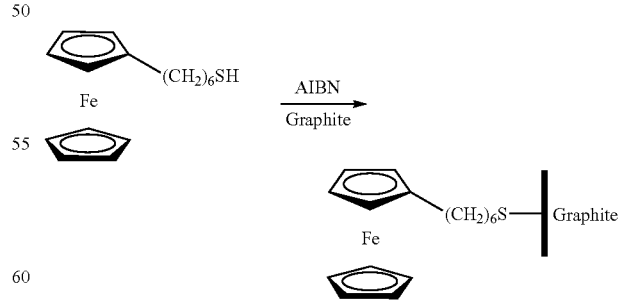

6-(Ferrocenyl)hexane thiol (100 mg, 0.33 mmol) was dissolved in anhydrous 1,2-dichloroethane (1 ml), graphite powder (20 mg) was added and the suspension purged with nitrogen for 10 mins. AIBN (20 mg, 0.12 mmol) was then added and the suspension heated at 45° C. for 16 hr. The derivatized graphite was collected, washed sequentially with 1,2-dichloroethane, N,N'-dimethylformamide, de-ionised water and methanol and then dried.

The reaction was repeated using carbon nanotubes. In both cases the derivatized carbon was deposited on a glassy carbon electrode and used as the working electrode of a cell with the same reference and counter electrodes as in Example 1. Buffer solutions with pH 4.2, 6.9 and 9.2 were used as electrolyte and square wave voltammetry was carried out.

Figure 3:
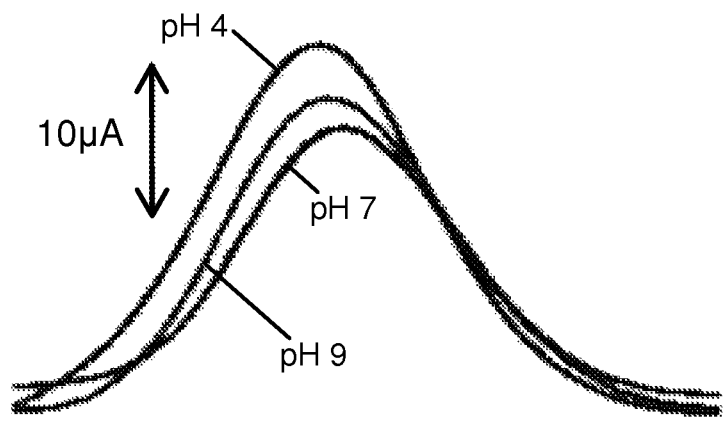
FIG. 3 shows the results of square wave voltammetry in Example 3.
Figure 3:
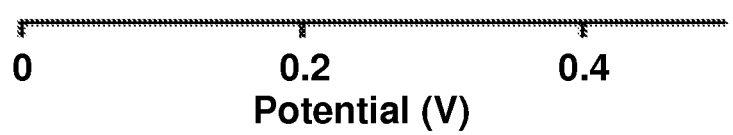

FIG. 3 shows the square wave voltammetric response of the derivatized graphite at the various pH values. Analysis of the results reveals an oxidative wave at +0.21 V (pH 4.2), +0.22 V (pH 6.9) and +0.21 V (pH 9.2). These results are consistent with the pH insensitive oxidation of ferrocene. The square wave voltammetry results with derivatized carbon nanotubes are not shown but were very similar. An oxidative wave was observed for each pH. These were at +0.17 V (pH 4.2), +0.17 V (pH 6.9) and +0.15 V (pH 9.2).

Cyclic voltammetry was carried out with the derivatized graphite to confirm the ferrocene attachment. It is well known that when a compound containing a ferrocene unit, is attached to the surface of an electrode, the intensities of the oxidative and reductive peaks respond linearly with scan rate. Cyclic voltammetry in pH 6.9 buffer as electrolyte was carried out at increasing scan rates (0.1 to 1 V/s). An oxidative peak was recorded at +0.23 V and a corresponding reductive wave at +0.16 V. Plots of oxidative and reductive peak current ($I_{pox}$ and $I_{pred}$) as a function of scan rate were linear, consistent with ferrocene being attached to the electrode.

EXAMPLE 4

A procedure similar to that of Example 3 was used to derivatize a solid edge-plane pyrolytic graphite (EPPG) electrode located within an inert plastic housing having an opening which exposed a 3 mm diameter disc of the electrode surface. The electrode was inserted through the septum of a 20 ml vial and suspended in the vial with the exposed surface immersed in a solution of 6-(ferrocenyl)hexane thiol and AIBN. The vial was heated at 50° C. for 16 hr. The electrode was then removed, washed with the same solvents as used in Example 3, and allowed to dry.

The derivatized electrode was examined by using it as the working electrode of a cell and carrying out square wave voltammetry with pH7 buffer as electrolyte. A strong oxidative wave is observed on the first scan consistent with oxidation of ferrocene attached to the electrode surface.

In a comparative experiment the same procedure was followed, but no AIBN was used. When the electrode was used for voltammetry, the oxidative wave was not observed.

Elaborating further on the nature and function of redox-active compounds which may be immobilized on an electrode, there are a number of redox active compounds which are sensitive to pH, so that when observed by voltammetry, the voltage at which there is maximum current flow (ie the voltage of the peak of the voltammetric wave) is dependent on pH. An electrode with such a compound immobilised on it can be used as a pH sensor.

Aromatic quinones which have such redox reactions are disclosed in WO2005/066618. The use of aromatic nitrogen compounds, which undergo irreversible reduction to hydroxylamine and thereafter undergo pH dependent reversible oxidation from hydroxylamine to nitroso compounds are disclosed in WO2010/001082.

In contrast, the oxidative and reductive peaks for ferrocene are substantially independent of applied voltage, so an electrode with a ferrocene compound immobilised on it can serve as a reference when measuring pH, as mentioned in WO2005/066618. A compound which is sensitive to an analyte and a reference compound may be immobilised on the same electrode or on separate electrodes.

An electrochemical reaction of a redox active compound may couple to a reaction of an analyte species of interest and act as a catalyst for its reaction. This analyte species can be determined by means of an amperometric measurement to measure any increase in the electric current which flows when the species is present: the magnitude of the increase in current provides a measure of the concentration of the species of interest.

One instance of this is determination of oxygen. If oxygen is present in an aqueous electrolyte, the electrochemical reduction of a quinone can couple to the reduction of that oxygen to water. The quinone then serves as a catalyst in the electrochemical reduction of oxygen and the concentration of oxygen can be determined from the increase in electric current compared with the current which flows in the absence of oxygen. The reactions can be represented as $$AQ+2H_2O+2e^- \rightarrow AQH_2+2OH^-$$

$$AQH_2+\tfrac{1}{2}O_2 \rightarrow AQ+H_2O$$

Under alkaline conditions, oxygen can be converted to hydrogen peroxide, the second step of the above reaction scheme then taking the form:

$$AQH_2+O_2 \rightarrow AQ+H_2O_2$$

If the electrochemical sensor is in contact with a non-aqueous liquid such as acetonitrile, the electrochemical reduction of a quinone can again couple to the reduction of oxygen, but the oxygen is reduced to superoxide, thus:

$$AQ+e^- \rightarrow AQ.^-$$

$$AQ.^- + O_2 \rightarrow AQ+O_2.^-$$

The redox reaction of ferrocene can couple to the oxidation of hydrogen sulphide to sulphur, so that the concentration of hydrogen sulphide can be determined from the increase in current compared to the current which flows in the absence of hydrogen sulphide. The use of ferrocene in the determination of hydrogen sulfide has been mentioned in WO2004/063743 and WO2010/001082. The reactions can be written as $$Fc \rightarrow Fc.^+ + e^-$$

$$Fc.^+ + HS^- \rightleftharpoons Fc + S + H^+$$

Ferrocene compounds can also be used in the determination of other analytes, as mentioned by Lawrence in Electroanalysis vol 18 pp 1658-1663 (2006).

As mentioned above, the derivatization reaction can be used to immobilize a compound by covalent attachment directly onto a carbon electrode. Another possibility is to attach the compound to particulate carbon such as graphite powder or carbon nanotubes and then immobilize this derivatized carbon on a carbon electrode. This may be done, as in the examples above, by evaporation of a suspension of the particles in a volatile solvent.

Another possibility is to pack such derivatized particulate carbon into a recessed cavity in an electrode. The empty recess might be filled with the derivatized carbon powder which would be mechanically compacted. The resulting void in the recess would then be refilled and compacted again. This would be repeated several times until the recess is full. The material would be pressed such that the carbon particles are packed into a dense matrix.

A further possibility is that derivatized carbon particles may be screen printed onto a substrate which may be an insulating material. Carbon particles derivatized with a second redox active compound which is insensitive to analyte/pH and which acts as a reference may be screen printed onto the same or another substrate. The particulate carbon may be combined with a binding material, which may be a conductive binding material such as a graphite-containing ink, and then screen printed onto the electrode. An external reference electrode may possibly be used with such a screen-printed electrode. One possible external reference is a silver/silver-chloride electrode. A screen-printed electrode may possibly carry such an external reference electrode on a portion of an insulating substrate. Particulate carbon derivatized with a redox active compound, mixed with a binder may also be applied to a working electrode by an inkjet-type process as an alternative to screen printing.

A screen-printed electrode may possibly be covered with a polymer film or coating. The polymer film or coating may, among other things, make the electrode more robust, prevent external adverse effects of the redox active compound(s), and allow for sterilization of the electrode without affecting the functionality of the electrode.

Some embodiments of electrochemical sensor include a temperature probe for measuring a temperature of the fluid, wherein the temperature measurement may be used to calibrate the electrochemical sensor.

An electrochemical sensor could be incorporated into a wide variety of tools and equipment. Possibilities include use in tools which are located permanently downhole, use in tools which are conveyed downhole, for instance at the head of coiled tubing or by drillpipe or on a wireline, use in underground, undersea or surface pipeline equipment to monitor liquid flowing in the pipeline, and use in a wide variety of process plant at the Earth's surface, including use in water treatment.

Figure 4:
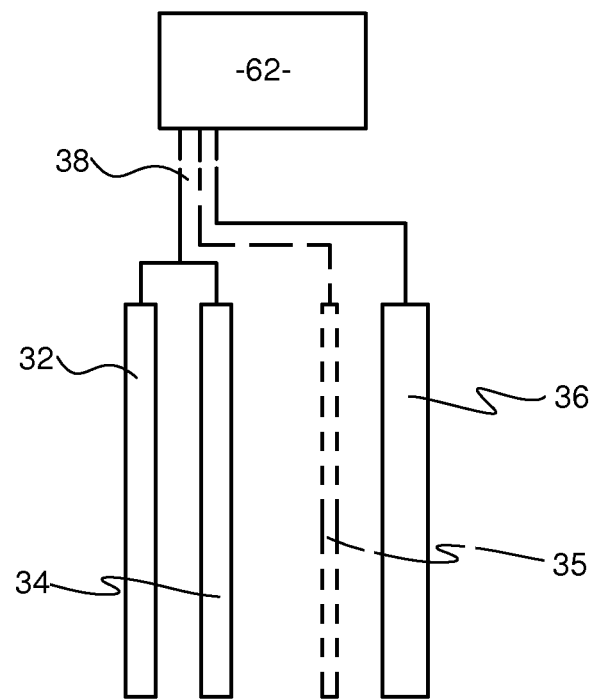
FIG. 4 is a diagrammatic illustration of the parts of an electrochemical sensor.

FIG. 4 diagrammatically illustrates apparatus which may be used in pH measurement. A working electrode 32 has carbon particles derivatized with a pH-sensitive redox active compound immobilized on its surface. A reference electrode 34 has carbon particles derivatized with a ferrocene compound immobilized on its surface. There is also counter electrode 36. All the electrodes are connected by cable or other wiring indicated at 38 to a potentiostat 62 or other control unit which provides electric power and measurement. This arrangement avoids a need for a standard reference electrode such as a standard calomel electrode. However, another possibility would be to provide such a standard electrode, as shown by broken lines at 35 and possibly dispense with the ferrocene electrode 34. The various electrodes are immersed in or otherwise exposed to fluid whose pH is to be measured.

Measuring apparatus may comprise electrode(s) which utilize derivatized graphite and also a control unit providing both electrical power and measurement. A control unit such as 62 may comprise a power supply, voltage supply, potentiostat and/or the like for applying an electrical potential to the working electrode 32 and a detector, such as a voltmeter, a potentiometer, ammeter, resistometer or a circuit for measuring voltage and/or current and converting to a digital output, for measuring a potential between the working electrode 32 and the counter electrode 36 and/or potential between the working electrode 32 and the reference electrode 34 or 35 and for measuring a current flowing between the working electrode 32 and the counter electrode 36 (where the current flow will change as a result of the oxidation/reduction of a redox species). The control unit may in particular be a potentiostat. Suitable potentiostats are available from Eco Chemie BV, Utrecht, Netherlands.

A control unit 62 which is a potentiostat may sweep a voltage difference across the electrodes and carry out voltammetry so that, for example, linear sweep voltammetry, cyclic voltammetry, or square wave voltammetry may be used to obtain measurements of the analyte using the electrochemical sensor. The control unit 62 may include signal processing electronics.

Figure 5:
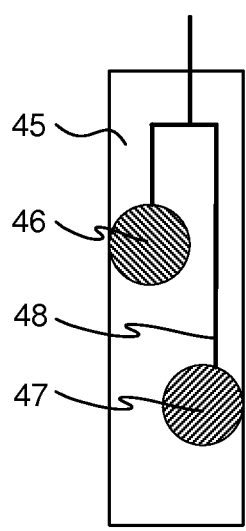
FIG. 5 shows another electrode construction.

FIG. 5 shows a possible variation. A conductive paste containing carbon derivatized with a pH sensitive redox compound is printed on one area 46 of an insulating substrate 45 to provide an electrode 32. A second conductive paste containing carbon derivatized with a pH insensitive ferrocene compound is printed on an area 47 as a reference electrode and both areas 46, 47 are connected together and connected to a cable 38 leading to a control unit by conductive tracks 48 on the substrate 45.

The electrodes 46, 47 may be screen printed using stencil designs to delineate the areas of the electrode. To form the working electrode, particulate carbon derivatized with a redox active compound may be mixed within a carbon-graphite ink and deposited on area 46 of a substrate 45 which may comprise polyester or other insulating polymer. To form the reference electrode a carbon-graphite ink may be deposited on area 47 of the substrate, then a reference electrode material, such as silver/silver-chloride may be deposited as a paste onto the area of deposited carbon. In some embodiments of electrode, a polymer coating may be applied on top of deposited materials (including deposited derivatized carbon). A polymer coating which is permeable to water and other small molecules may prevent derivatized carbon from becoming detached from the working electrode, but still allow for interactions between an analyte and a redox active compound on the working electrode. For example a polymer coating may comprise a polysulphone polymer or a polystyrene polymer.

Figure 6:
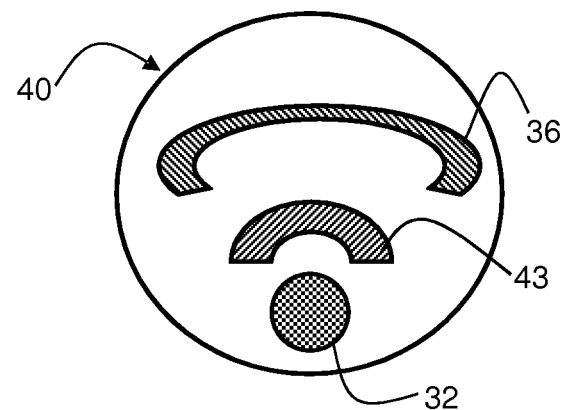
FIG. 6 illustrates the geometrical surface layout of the surface of a sensor.

FIG. 6 shows a possible geometric configuration or layout for the surface 40 of a sensor which is exposed to the fluid to be tested, which may, merely by way of example be a wellbore fluid. The surface includes a disk shaped working electrode 32, a second electrode 43, which may be a ferrocene electrode or an external reference electrode such as a silver/silver chloride electrode, and a counter electrode 36.

Figure 7:
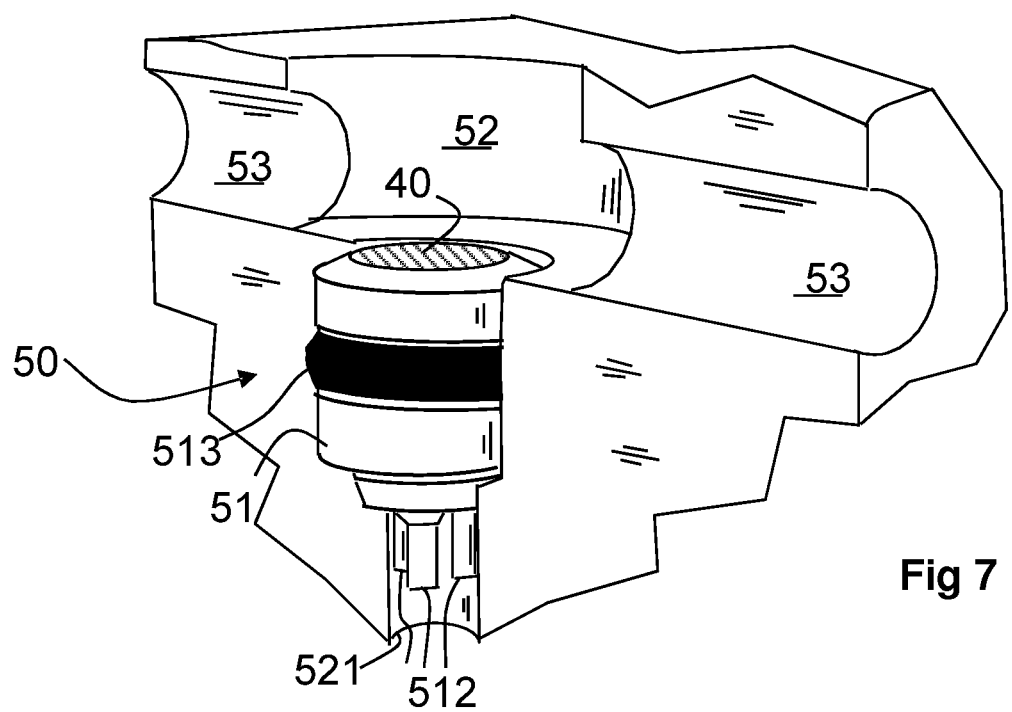
FIG. 7 is a perspective view, partially cut-away, of an electrochemical sensor incorporating the surface of FIG. 6.

A schematic of a microsensor 50 incorporating such a surface is shown in FIG. 7. The body 51 of the sensor is fixed into the end section of an opening 52. The body carries the electrode surface 511 and contacts 512 that provide connection points to voltage supply and measurement through a small channel 521 at the bottom of the opening 52. A sealing ring 513 protects the contact points and electronics from the fluid to be tested that passes under operation conditions through the sample channel 53.

Figure 8:
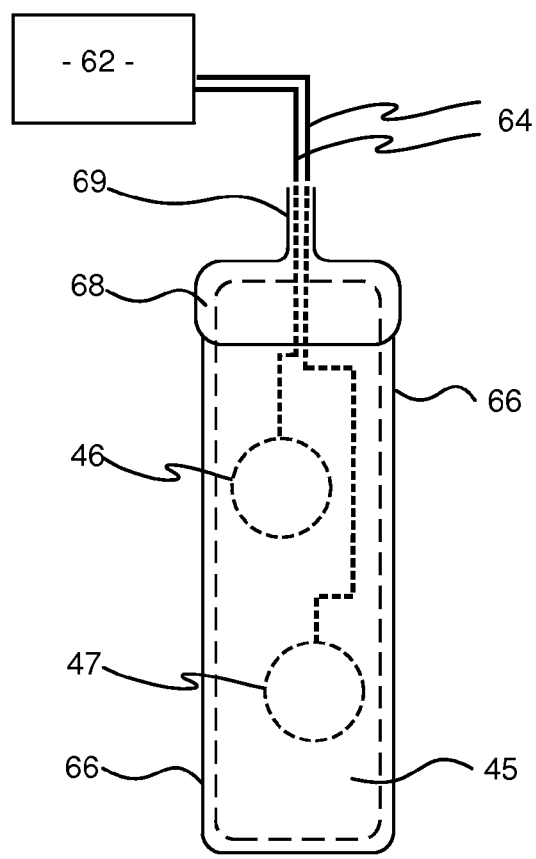
FIG. 8 illustrates a working electrode covered at least in part by a polymer layer.

FIG. 8 shows a substrate 45 carrying a working electrode on an area 46 and a reference electrode on an area 47. These are not connected together but are connected by separate conductors within a cable 64 to a potentiostat 62 which may be a handheld device. After deposition of electrode materials onto the substrate 45, the substrate and deposited materials were coated with a permeable polymer layer indicated by reference 66. Methods to deposit the polymer in a generally uniform layer include spin coating, dip coating and application using solvent evaporation. One end of the coated substrate has an impermeable covering 68 which merges with the sheath 69 of the cable 64.

Figure 9:
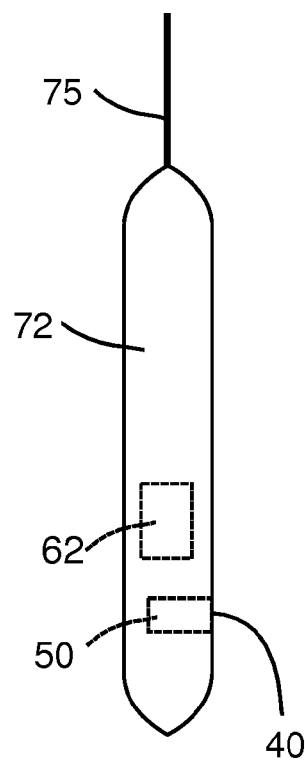
FIG. 9 is a diagrammatic illustration of a cable-suspended tool for testing water.

One application of an electrochemical sensor may lie in the monitoring of underground bodies of water for the purposes of resource management. Using monitoring wells drilled into the aquifers, one or more sensors may be deployed on a cable from the surface. The sensor(s) may be in place for a relatively short duration (as part of a logging operation) or a longer term (as part of a monitoring application). FIG. 9 illustrates a tool for investigating subterranean water. This tool has a cylindrical enclosure 72 which is suspended from a cable 75. A sensor unit such as the sensor 50 shown in FIG. 7 is accommodated within the enclosure 72 so that its surface 40 is exposed to the subterranean water. The tool also encloses also encloses a unit 62 for supplying voltage to the electrodes of the sensor 50, measuring the current which flows and transmitting the results to the surface.

The sensor may be a pH sensor. Suspending such a device on a cable within producing wells may provide information on produced water quality. Also, the pH sensor may be deployed in injection wells, e.g. when water is injected into an aquifer for later retrieval, where pH may be used to monitor the quality of the water being injected or retrieved.

Figure 10:
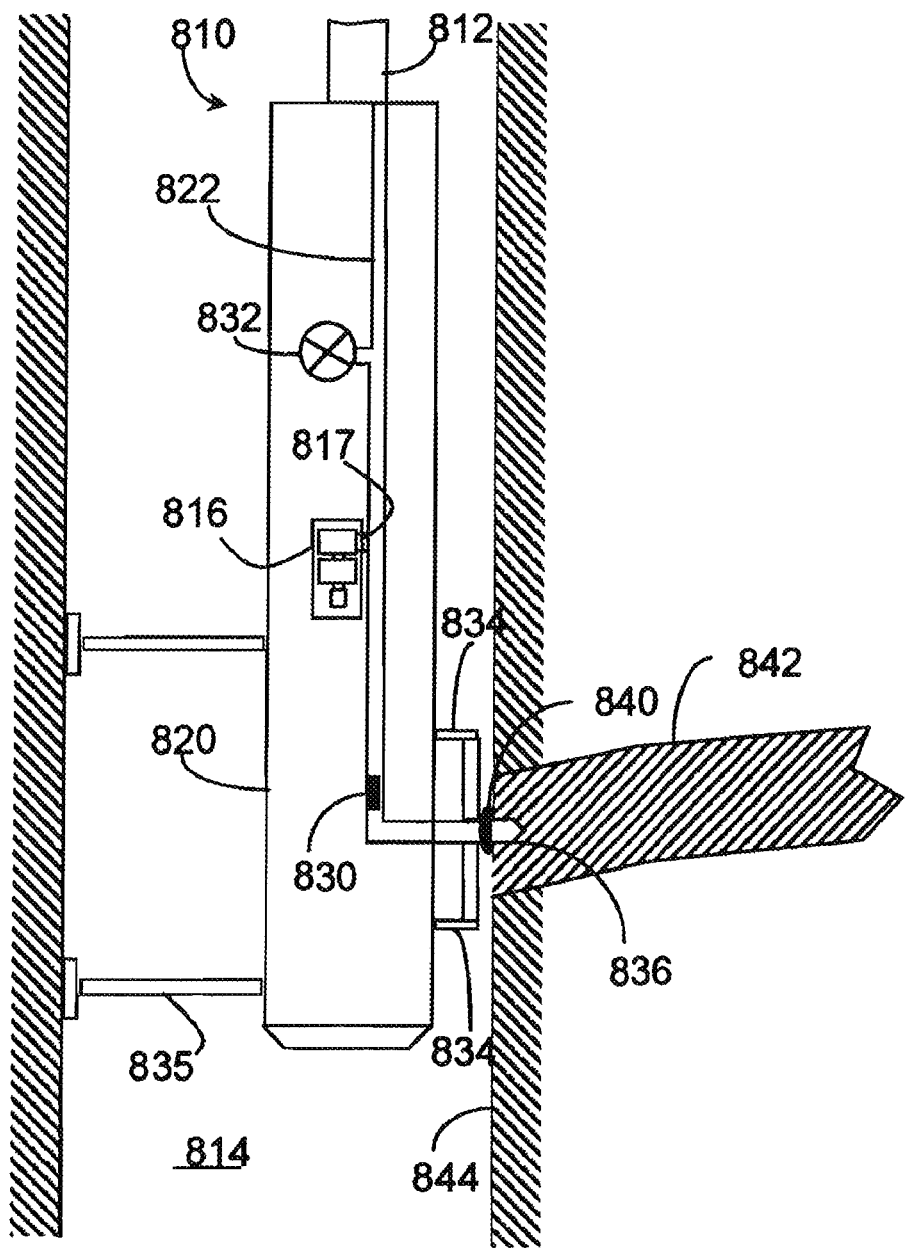
FIG. 10 illustrates an example of an electrochemical sensor, as part of a wireline formation testing apparatus in a wellbore.

FIG. 10 shows a formation testing apparatus 810 held on a wireline 812 within a wellbore 814. The apparatus 810 is a well-known modular dynamic tester (MDT, Trade Mark of Schlumberger) as described in the co-owned U.S. Pat. No. 3,859,851 to Urbanosky, U.S. Pat. No. 3,780,575 to Urbanosky and U.S. Pat. No. 4,994,671 to Safinya et al., with this known tester being modified by introduction of an electrochemical analyzing sensor 816 substantially similar to sensor 50 of FIG. 7 The modular dynamics tester comprises body 820 approximately 30 m long and containing a main flowline bus or conduit 822. The analysing tool 816 communicates with the flowline 822 via opening 817. In addition to the novel sensor system 816, the testing apparatus comprises an optical fluid analyser 830 within the lower part of the flowline 822. The flow through the flowline 822 is driven by means of a pump 832 located towards the upper end of the flowline 822. Hydraulic arms 834 and counterarms 835 are attached external to the body 820 and carry a sample probe tip 836 for sampling fluid. The base of the probing tip 836 is isolated from the wellbore 814 by an o-ring 840, or other sealing devices, e.g. packers.

Before completion of a well, the modular dynamics tester is lowered into the well on the wireline 812. After reaching a target depth, i.e., the layer 842 of the formation which is to be sampled, the hydraulic arms 834 are extended to engage the sample probe tip 836 with the formation. The o-ring 840 at the base of the sample probe 836 forms a seal between the side of the wellbore 844 and the formation 842 into which the probe 836 is inserted and prevents the sample probe 836 from acquiring fluid directly from the borehole 814.

Once the sample probe 836 is inserted into the formation 842, an electrical signal is passed down the wireline 812 from the surface so as to start the pump 832 and the sensor systems 816 and 830 to begin sampling of a sample of fluid from the formation 842. The electrochemical sensor 816 can then measure the pH or concentration of another analyte such as hydrogen sulfide in the formation effluent.

While the preceding uses of an electrochemical sensor are in the hydrocarbon and water industries, embodiments of electrochemical sensor incorporating derivatized carbon may be used for detecting an analyte in a whole host of industries, including food processing, pharmaceutical, medical, water management and treatment, and biochemical industries, as well as research laboratories. A polymer coating may prevent escape of derivatized carbon particles from an electrode into the fluid around it, but still allow for interactions between an analyte and one or more redox active compounds on the electrode.

Derivatization of carbon may also be carried out for applications other than electrochemical sensors. Some possibilities arise when carbon is to be incorporated into a composition. One instance is to protect rubbers against degradation through attack by radical species leading to damage to the chemical structure of the elastomer; for this purpose rubber may incorporate a carbon filler which has been derivatized with one or more radical scavengers which could prolong the lifetime of the rubber. Similarly, in other circumstances where a polymer or elastomer composition incorporates a carbon filler, additives such as plasticisers can be grafted onto the carbon filler to prevent them from being leached from the composition. Furthermore the carbon filler can be derivatized in order to enable it to bond chemically with the polymer or elastomer and increase the mechanical strength of the composition.

A persistent problem in the use of single walled carbon nanotubes (SWCNTs) in some nanoscale electronic devices such as field effect and other transistors is the presence of so-called metallic tubes generated during their synthesis. The resulting high electrical conductivity can preclude their use in transistors. It has been found that derivatization of the carbon can suppress unwanted high conductivity and enable SWCNTs to be used in semiconductor devices. Kanungo et al. *Science*, vol 323, pages 234-237 (2009) derivatized metallic SWCNTs with perfluoro-2(2-fluorosulfonylethoxy) propyl vinyl ether (PSEPVE) using a [2+2] cycloaddition reaction, which resulted in a large decrease in electrical conductivity. The derivatisation methods disclosed herein could be used to reduce the electrical conductivity of SWCNTs. For example, the thiol derivatisation reaction can be used to attach a —$OCF_2CF(CF_3)OCF_2CF_2SO_2F$ group to carbon, thus:

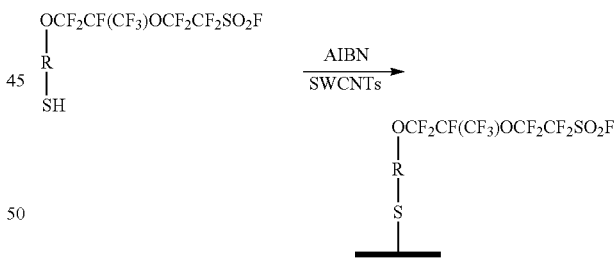

where R is an organic group.

It will be appreciated that the example embodiments described in detail above can be modified and varied within the scope of the concepts which they exemplify. Features referred to above or shown in individual embodiments above may be used together in any combination as well as those which have been shown and described specifically. Accordingly, all such modifications are intended to be included within the scope of this disclosure as defined in the following claims.

The invention claimed is:
1. A process for derivatization of an elemental carbon surface, the process comprising:

exposing the carbon surface to a reaction mixture containing a thiol of the general formula Y—SH wherein Y is an organic moiety and a free radical initiator; and inducing decomposition of the initiator to free radicals, whereby Y—S-moieties become covalently attached to the carbon surface.

2. A process according to claim 1 wherein Y comprises a compound having at least one functional group which can be converted electrochemically between reduced and oxidized forms.

3. A process according to claim 2 wherein Y comprises an aromatic quinone or aromatic nitro compound.

4. A process according to claim 2 wherein Y comprises a compound with at least two fused aromatic rings with oxygen or nitrogen-containing substituents, at least some of the said substituents being convertible between reduced and oxidized forms.

5. A process according to claim 1 wherein Y comprises ferrocene or a compound thereof.

6. A process according to claim 1 wherein the free radical initiator is an azo compound.

7. A process according to claim 1 wherein Y comprises a redox-active group able to undergo electrochemical redox reaction and the process further comprises utilizing the derivatized carbon with Y—S-moieties covalently attached thereto as at least part of an electrode and connecting the electrode to measuring apparatus to apply voltage to the electrode and measure current flow through the electrode, thereby incorporating the modified elemental carbon into measuring apparatus.

8. A process according to claim 1 wherein Y comprises a redox-active group able to undergo electrochemical redox reaction and the process further comprises: utilizing the derivatized carbon with Y—S-moieties covalently attached thereto as at least part of an electrode; applying voltage to the electrode while it is immersed in solution and measuring current flow through the electrode; and processing the measurements to give a determination of analyte concentration in the solution.

9. A method of determining a concentration of an analyte in a liquid, the method comprising:
    contacting the liquid with at least two electrodes, wherein one electrode of the at least two electrodes comprises elemental carbon in solid form derivatized so as to have redox-active species attached thereto through sulfur atoms covalently bound to the species and to the elemental carbon;
    applying potential to the one electrode and varying the potential over a range sufficient to bring about at least one oxidation and/or reduction of the redox active compound;
    measuring potential or potentials corresponding to the at least one oxidation and/or reduction; and
    processing the measured potential or potentials to give a determination of analyte concentration;
    wherein the elemental carbon in solid form is derivatized by exposing a surface of the carbon to a reaction mixture containing a thiol of the general formula Y—SH wherein Y is an organic moiety and a free radical initiator, and inducing decomposition of the initiator to free radicals, whereby Y—S—moieties become covalently attached to the carbon surface.

10. A method according to claim 9 wherein the liquid is aqueous.

11. A method according to claim 10 which is a method for measuring pH of the aqueous liquid.

* * * * *